United States Patent [19]
Jacobsen et al.

[11] Patent Number: 5,588,688
[45] Date of Patent: Dec. 31, 1996

[54] ROBOTIC GRASPING APPARATUS

[75] Inventors: Stephen C. Jacobsen, Salt Lake City; Dwight Potter, Stansbury Park; Fraser Smith, Salt Lake City, all of Utah

[73] Assignee: Sarcos, Inc., Salt Lake City, Utah

[21] Appl. No.: 272,196

[22] Filed: Jul. 8, 1994

Related U.S. Application Data

[63] Continuation-in-part of Ser. No. 58,690, May 7, 1993, Pat. No. 5,328,224, which is a continuation of Ser. No. 963,831, Oct. 20, 1992, abandoned, which is a continuation of Ser. No. 563,399, Aug. 6, 1990, Pat. No. 5,172,951.

[51] Int. Cl.$^6$ ........................................... B25J 15/10
[52] U.S. Cl. ..................... 294/106; 294/88; 294/902; 901/37; 901/39
[58] Field of Search .................. 294/88, 104, 106, 294/115, 902; 901/31, 37, 39; 623/64

[56] References Cited

U.S. PATENT DOCUMENTS

| | | | |
|---|---|---|---|
| 3,069,761 | 12/1962 | Sommer | 294/106 |
| 4,332,038 | 6/1982 | Freeland | 623/64 |
| 4,368,913 | 1/1983 | Brockmann et al. | 294/106 |
| 4,377,305 | 3/1983 | Horvath | 294/106 |
| 4,545,723 | 10/1985 | Clark | 901/31 |
| 4,696,503 | 9/1987 | Collodel | 294/88 |
| 4,824,155 | 4/1989 | Jacobsen | 294/88 |
| 4,921,293 | 5/1990 | Ruoff et al. | 623/64 |
| 5,217,274 | 6/1993 | Iichuk | 294/88 |

FOREIGN PATENT DOCUMENTS

| | | | |
|---|---|---|---|
| 1399115 | 5/1988 | U.S.S.R. | 294/115 |

*Primary Examiner*—Dean Kramer
*Attorney, Agent, or Firm*—Thorpe North & Western

[57] ABSTRACT

A robotic grasping manipulator includes a support base, a pair of fingers disposed on the base which extend forwardly a certain distance therefrom, and a two-degree of freedom elongate thumb. The thumb is pivotally attached at a proximal end to the base to extend generally forwardly therefrom, and terminates in a distal end tip which may be moved vertically and laterally with respect to the fingers to thereby enable holding objects between one or both fingers and the thumb. The fingers are moveable in a plane toward or away from each other, and include tip sections which are pivotable downwardly in a direction generally normal to the plane of movement of the fingers. A unique linkage apparatus intercouples the fingers with the base such that a non-pivotal, back-and-forth-moving piston rod can be used to move the fingers. The fingers contain gripping structure including rigid, pointed protuberances interleaved with flexible, blunt protuberances which are longer than the rigid protuberances. With the two-degree of freedom movement of the thumb and the movement of the fingers and their tip sections, a variety of different shaped objects may be grasped and held between the two fingers and thumb.

39 Claims, 11 Drawing Sheets

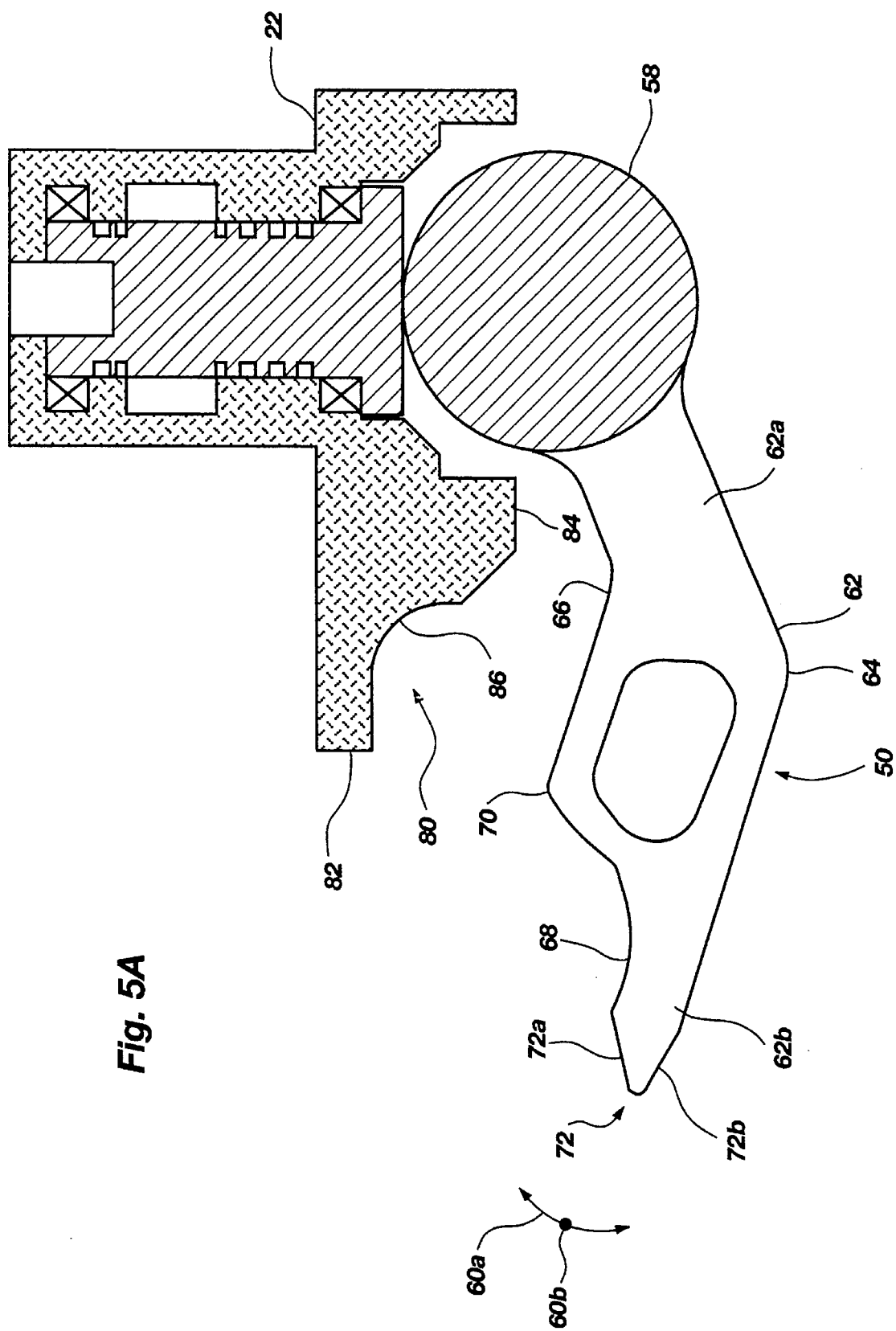

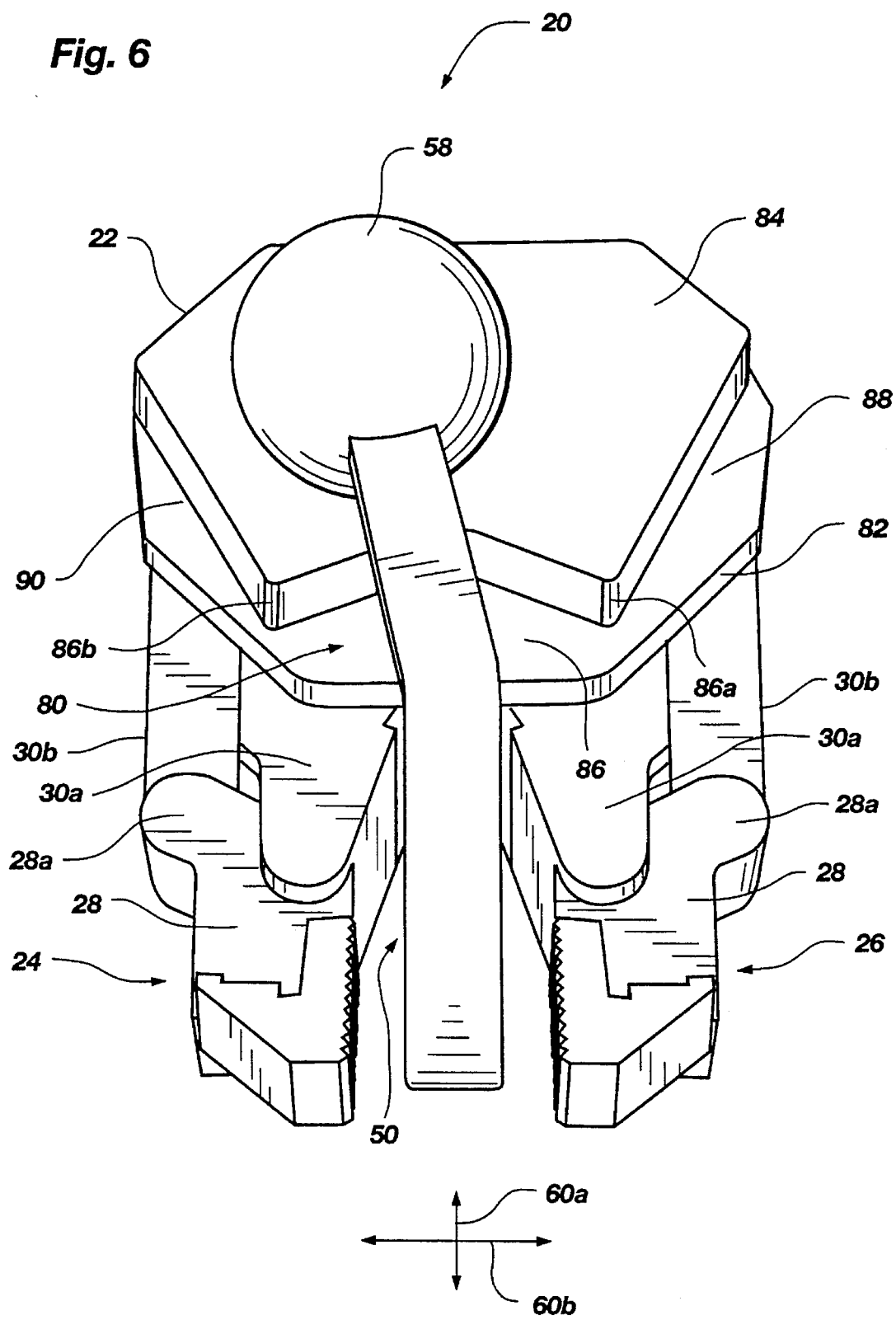

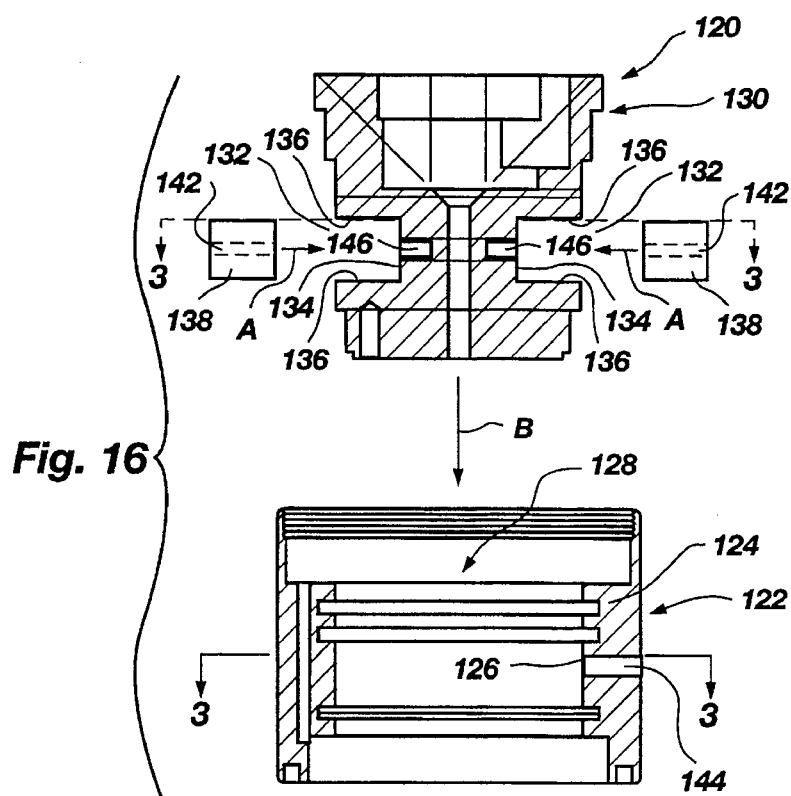
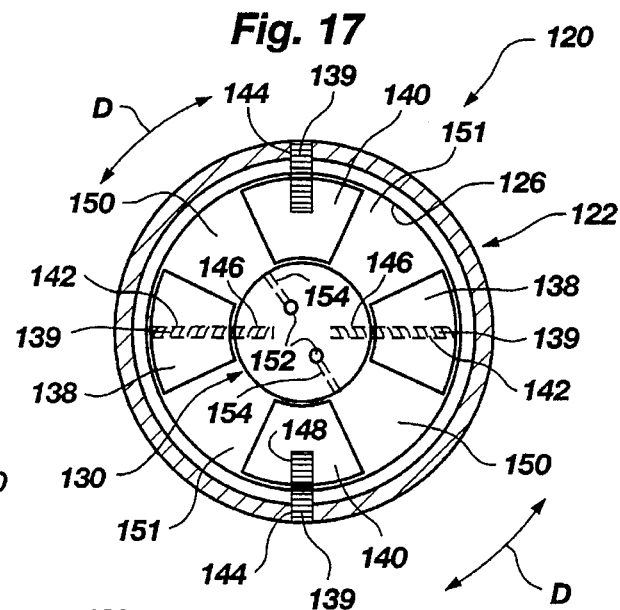
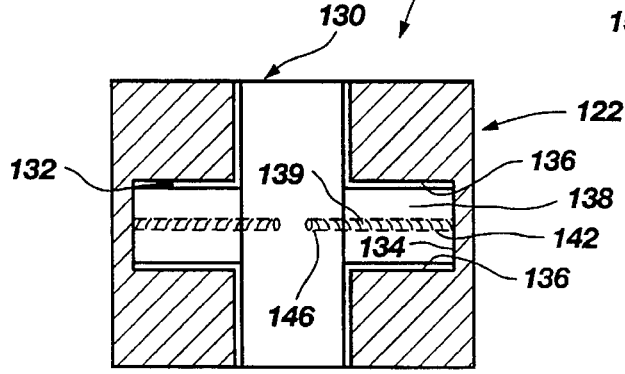

ROBOTIC GRASPING APPARATUS

This is a continuation-in-part of U.S. patent application Ser. No. 08/058,690 filed on May 7, 1993 by the same title now U.S. Pat. No. 5,328,224, which is a continuation of U.S. patent application Ser. No. 07/963,831, filed on Oct. 20, 1992 now abandoned, which was a continuation of U.S. patent application Ser. No. 07/563,399filed on Aug. 6, 1990, which was issued as U.S. Pat. No. 5,172,951.

BACKGROUND OF THE INVENTION

1. The Field of the Invention

This invention relates to robotic apparatus and more particularly to grasping and manipulating apparatus.

2. The Prior Art

Robotic devices and implements have been used in a variety of fields where direct human involvement is either too hazardous, too inefficient, or too monotonous and tiring. Examples of such fields include manufacturing where robots are used to carry out pickup and assembly of parts, welding, nailing and riveting, etc., handling of hazardous material such as radioactive products where direct human handling could pose a health risk, and remote handling or manipulation of articles, control panels, or other structures where on-site location of humans is desirable or possible. Also, more sophisticated, efficient and dexterous robotic apparatus is being sought for use as artificial limbs. This is especially true for implements to enable grasping and holding in a manner similar to the grasping and holding ability of the human hand.

Robotic grasping implements currently available range from the simple two jaw gripping device formed similar to the jaws of a pair of pliers, to the more complicated artificial hands having three or four fingers and a thumb which may be operated to curl about objects to be grasped. Both the simple and complicated grasping implements are characterized by a number of disadvantages. While larger objects can oftentimes be handled, smaller or thinner objects cannot be, especially if such objects must be picked up from a flat surface for example. Also, the number of positions or orientations in which graspable objects can be held is generally very limited with currently available grasping implements. A further disadvantage of prior art robotic devices is an inability to conform around a frangible object for gripping purposes without breaking the object.

SUMMARY OF THE INVENTION

It is an object of the invention to provide robotic grasping apparatus with anthropomorphic characteristics.

It is another object of the invention to provide a simple and easy to control robotic grasping apparatus.

It is a further object of the invention to provide a grasping apparatus which is capable of holding and picking up small and thin objects as well as larger objects.

It is yet another object of the invention to provide a grasping apparatus capable of conformably wrapping around a frangible object for gripping purposes without breaking the object.

It is an additional object of the invention to provide a versatile grasping apparatus for holding objects having a variety of sizes and shapes.

It is still another object of the invention to provide such an apparatus capable of holding objects in a variety of positions and orientations.

The above and other objects of the invention are realized in a specific illustrative embodiment of a robotic grasping apparatus which includes a support base and first and second fingers attached at proximal ends to the support base to extend forwardly therefrom. The fingers are selectively moveable in a plane toward or away from one another.

In accordance with one aspect of the invention, each of the fingers includes a base section attached at one end to the support base and a tip section pivotally attached at a pivot end to the other end of the base section. Each tip section is pivotable downwardly in a direction generally normal to the plane of movement of the fingers.

In accordance with another aspect of the invention, each of the fingers includes a facing, gripping side. Each gripping side includes a first plurality of substantially rigid projections extending outwardly therefrom. A second plurality of substantially flexible, resilient projections is interleaved with said first projections and extends outwardly from said gripping side a greater distance than said first projections.

In accordance with a further aspect of the invention, a first linkage member intercouples the first finger with the support base, and a second linkage member intercouples the second finger with the support base. The linkage members are moveable to cause the fingers to move toward or away from each other. A connecting link is pivotally connected to the first and second linkage means and to a piston rod. The piston rod is selectively moveable generally linearly in a back and forth fashion to thereby cause the connecting link, the first and second linkage means, and the first and second fingers, respectively, to move.

In accordance with still another aspect of the invention, an elongate thumb is pivotally attached at a proximal end to the support base to pivot a distal end toward and away from the plane of movement of the fingers. The thumb includes an end hook for lifting objects from surfaces. The distal end is selectively moveable into contact with one or both finger tips and with either side of said finger tips, and to non-contacting positions on either side of the fingers. This enables versatile and firm gripping of a plurality of objects of various sizes and shapes in either a pinching or cradling manner. The thumb is further shaped to allow a cradling grasp of objects such that the apparatus essentially conforms around and cages an object to thereby constrain it without relying solely upon frictional normal forces to constrain the object.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the following detailed description presented in connection with the accompanying drawings in which:

FIG. 5A is a side view of a thumb of a robotic grasping apparatus made in accordance with the principles of the present invention;

FIG. 6 is a perspective view of the robotic grasping apparatus of FIG. 5B in an inverted position;

FIG. 16 is an exploded, side cross sectional view of a rotor actuator of the robotic grasping apparatus of FIGS. 1–15, made in accordance with the present invention;

FIG. 17 is plan, partial cross sectional view of the rotor actuator of FIG. 16 in an assembled form, taken along sections 3—3; and FIG. 18 is a side, partial cross sectional view of an alternative embodiment of the rotor actuator of FIGS. 16–17.

DETAILED DESCRIPTION

Figure 1A:
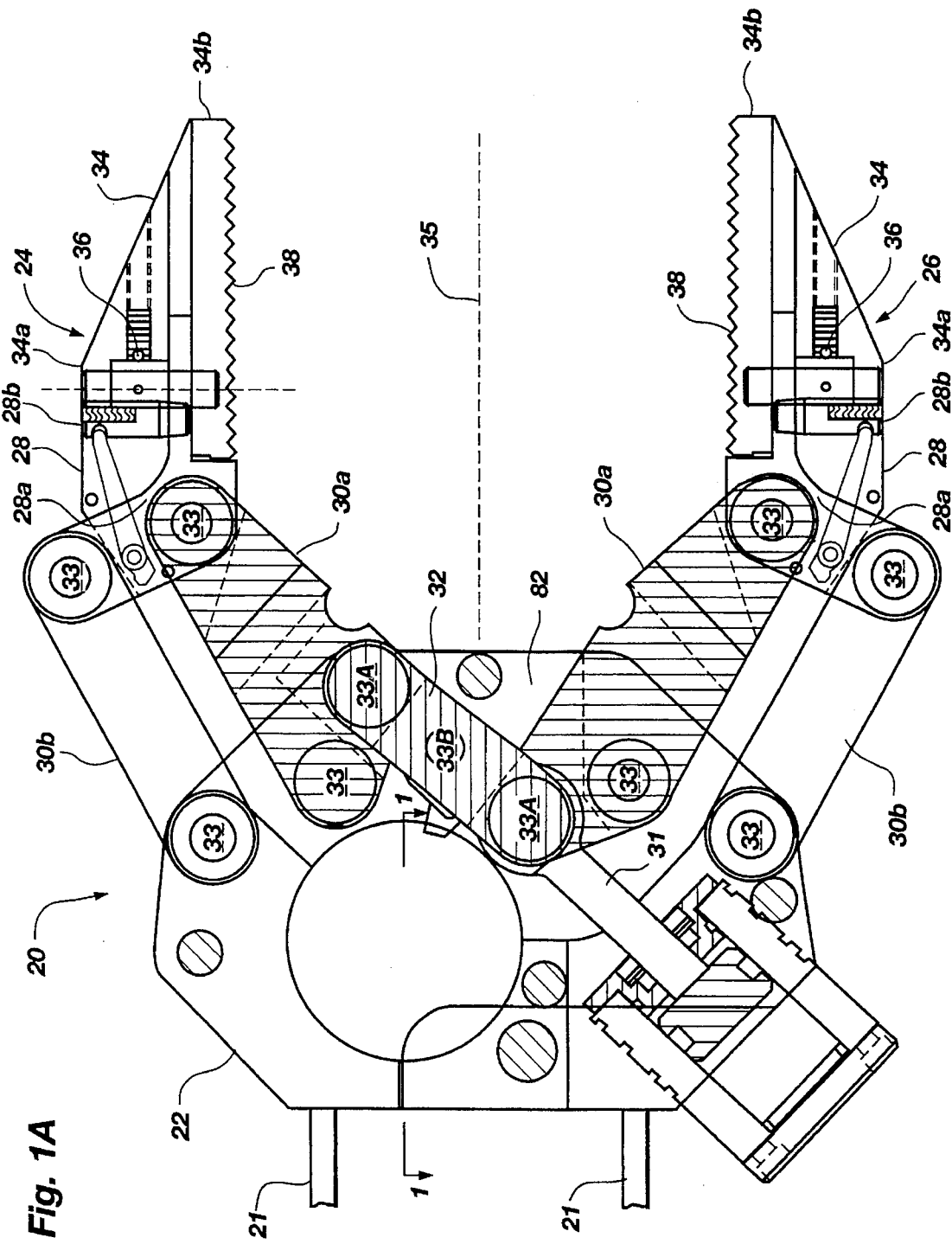
FIG. 1A is a plan view showing interior components of a robotic grasping apparatus in an open position, made in accordance with the principles of the present invention.

Referring to FIGS. 1–6, there are shown various views of one specific illustrative embodiment of a robotic grasping apparatus, generally designated at 20, illustrating the principles of the present invention. This apparatus 20 includes a housing or base 22 from which first and second fingers 24 and 26 project. The base 22 contains control mechanisms for controlling the movement of the fingers. The base 22 might illustratively be joined to a jointed robotic arm or other similar robotic structure by support bars 21 to enable positioning the grasping apparatus in different orientations. Such robotic arms are known in the art.

In a preferred embodiment, the fingers 24 and 26 extend generally forwardly from the base 22 and involve identical mounting techniques and structure. The fingers each include a base section 28 intercoupled at a proximal end 28a to the base 22 by first and second parallel link members 30a and 30b, at pivotal connections 33. A link connector 32 is pivotally connected to the first link members 30a at pivotal connections 33A, and to a piston rod 31 at pivotal connection 33B. This linkage interconnection permits the piston rod 31 to be confined to a generally linear, back and forth movement to thereby move the link connector 32, which in turn causes the first link members 30a to move, which causes the fingers 24 and 26 to move in a plane toward or away from one another. The second link members 30b are caused to move in tandem with the fingers 24 and 26. The fingers 24 and 26 thereby provide a two-jaw parallel grip instead of a two-jaw pinching grip as in prior art grippers which grip similar to a pair of pliers.

Figure 1B:
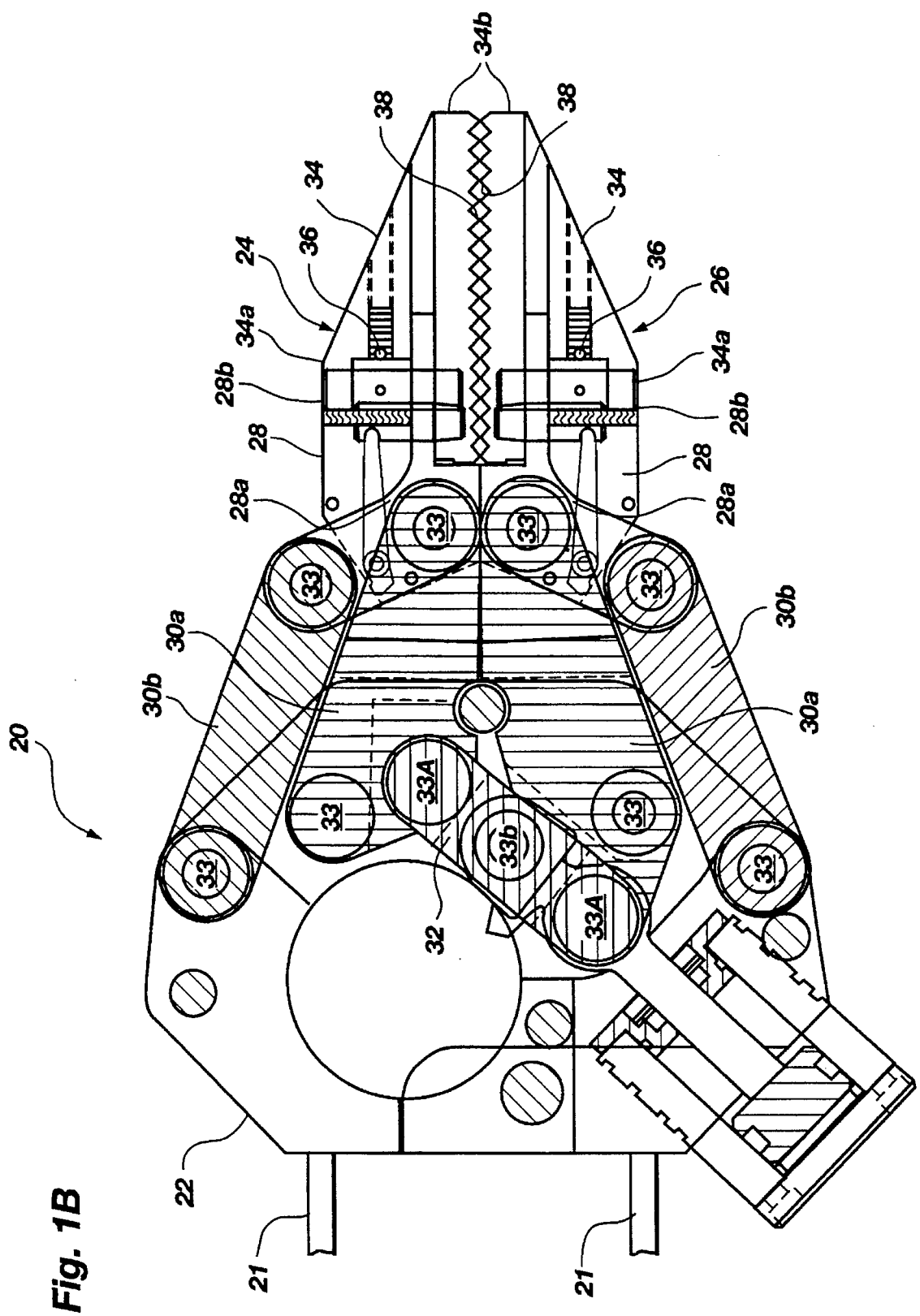
FIG. 1B is a plan view of the apparatus of FIG. 1A in a closed position.
Figure 2:
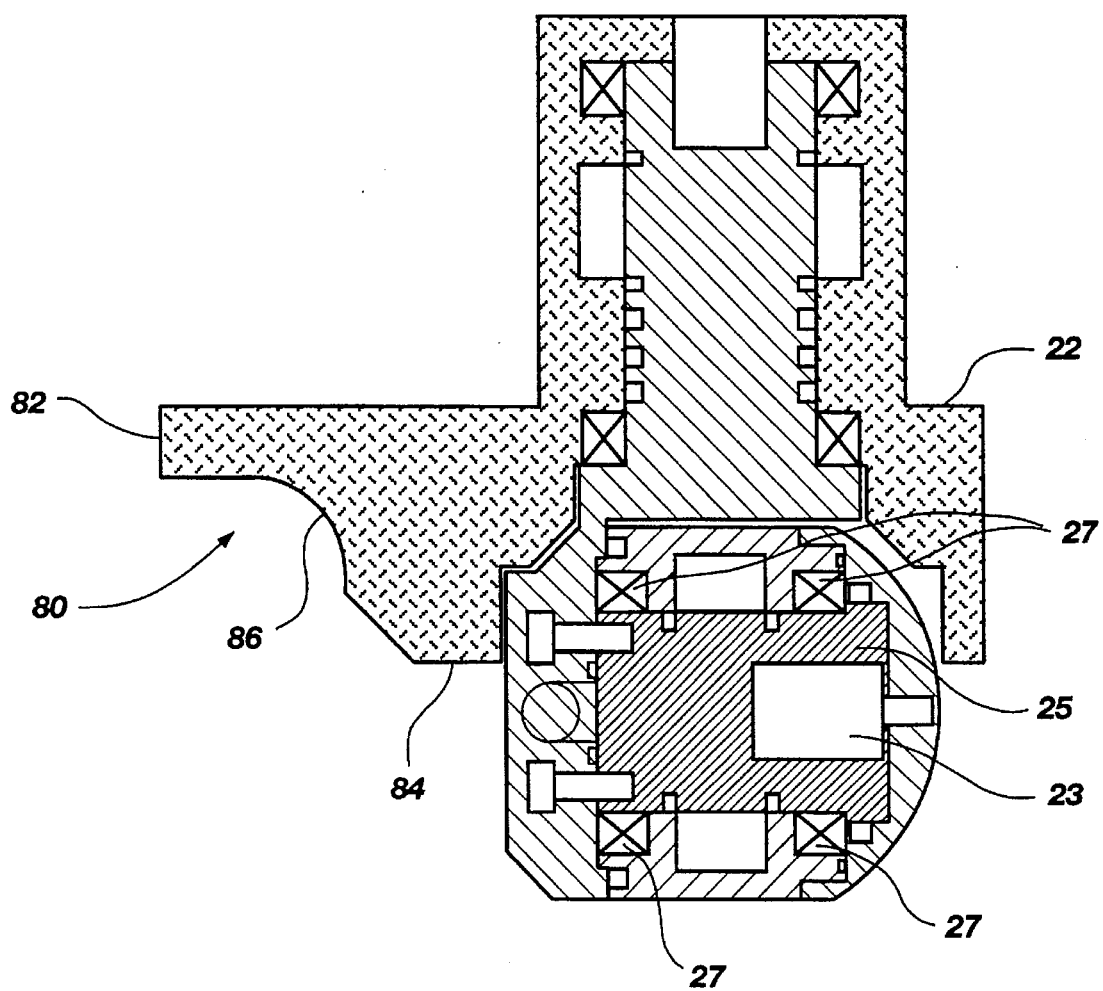
FIG. 2 is a side, cross sectional view of a portion of the apparatus of FIG. 1A, taken along section 1—1 to illustrate load and position sensors of the apparatus.
Figure 3:
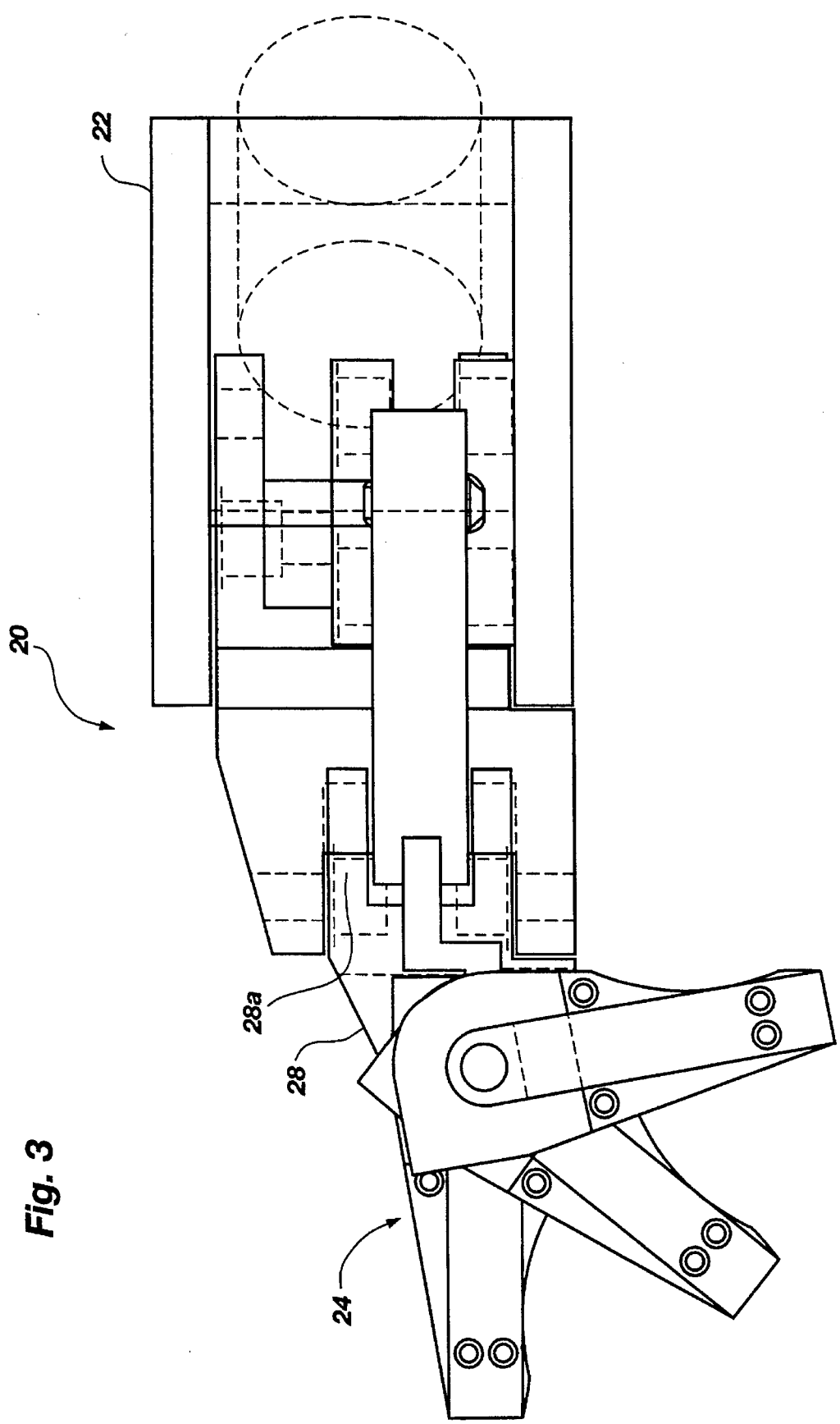
FIG. 3 is a side view of the apparatus of FIG. 1A, showing stages of movement of a finger tip thereof.

The combination of the geometric configuration of the first link members 30a with the connection points 33 relating thereto obviates the need for a rotating piston rod as in many actuating mechanisms. It will be appreciated that the first link members 30a are shaped differently as shown in FIGS. 1A and 1B in order to transfer the linear pulling and pushing force from the piston 31 first to the fingers 24 and 26 such that said fingers move in opposite directions. The first link members 30a of each finger 24 and 26 are positioned adjacent one another in the plane of movement of the fingers. The connecting link 32 is pivotally coupled to the adjacent first link members 30a as shown, and also to the piston rod 31 at pivotal connection 33B. Although the pivotal connection at 33B enables the connecting link 32 to pivot relative to the piston rod 31, it is shown by the relative positions of FIGS. 1A and 1B that the connecting link pivots little if at all relative to the piston rod 31. The connecting link 32 thus moves substantially in a linear back and forth motion with the piston rod 31, and thus along a line which extends between the two adjacent first link members 30a at an angle with a midline 35 between the adjacent first link members 30a.

It will be appreciated by those skilled in the art that the described linkage assembly eliminates the need for sliding joints and pivoting cylinders found in other robotic gripping apparatus. For example, upon reversal of some prior art actuating mechanics, the combined action of the sliding joints and/or pivoting cylinders results in a point of zero load while the parts re-engage in the opposite direction, preventing effective diagnosis and evaluation of force capacity. It will be appreciated that the linkage assembly of the present invention provides a closed force loop regardless of directional movement change of the piston rod 31, because the piston rod need only move linearly and without the aid of sliding parts to actuate opening and closing of the fingers 24 and 26.

Each finger also includes a tip section 34 which is pivotally attached at a pivot end 34a to the other end 28b of the base section 28. The tip section 34 is pivotable downwardly in a direction generally normal to the plane of movement of the fingers 24 and 26. A ball detent apparatus 36 pivotally connects the respective pivot end 34a with a respective other end 28b in each finger as known in the art for locking the tip section 34 in a plurality of different positions pivoted downwardly from the plane of movement of the fingers. The tip sections 34 are manually manipulated into the different positions by pressing distal ends 34b of said tip sections 34 against a surface. Once a tip section 34 is manipulated into a pivoted position with respect to its base section 28, the ball detent apparatus 36 holds it in the pivoted position. This allows the advantage of various tip angles and thereby increases the number of possible grips the fingers can achieve without the addition of another actuated joint.

Figure 4A:
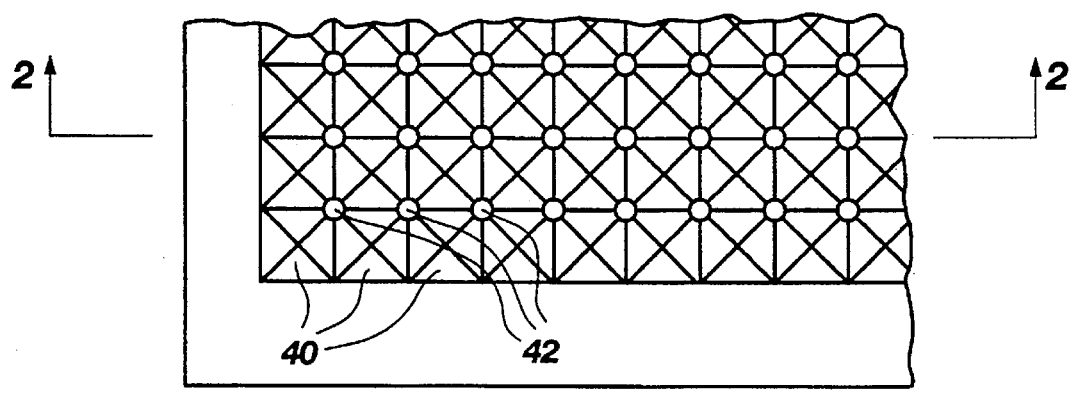
FIG. 4A is a partially fragmented view of a portion of the fingers of FIG. 1A.
Figure 4B:
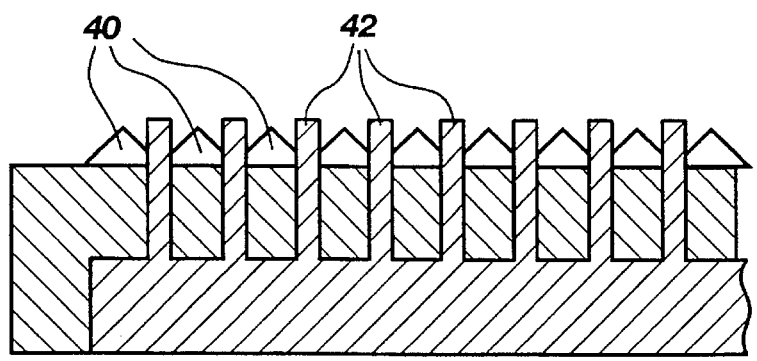
FIG. 4B is a side, cross sectional view of the finger portion of FIG. 4A, taken along section 2—2.

The fingers 24 and 26 further include gripping structure 38 as will now be explained with reference to FIGS. 4A and 4B. The gripping structure 38 includes a first plurality of substantially rigid protuberances 40, and a second plurality of substantially flexible, resilient protuberances 42 interleaved with said first plurality of rigid protuberances. Each of the first and second pluralities of protuberances 40 and 42 extend outward from each finger toward the other finger in a generally parallel direction relative to movement of the fingers 24 and 26.

The flexible, resilient protuberances 42 are longer than the rigid protuberances 40 and thus project farther outward from the fingers. The rigid protuberances 40 are preferably made from a metal alloy, and are preferably shaped in a four-sided pyramidal configuration terminating in a point for holding higher weight, less fragile objects. The flexible protuberances 42 are preferably made from a non-skid polymer composition and are preferably shaped to terminate generally in a blunt surface for contacting and holding lower weight, more fragile objects.

The rigid and flexible protuberances 40 and 42 of the gripping structure 38 disposed on the finger 24 and 26 provide many advantages. For example, the flexible protuberances 42 are better able to distribute gripping loads throughout the finger, thereby minimizing unstable moments. The flexible protuberances 42 are also less damaging to the grasp objects and require lower forces to achieve a stable grasp. The rigid protuberances 40 are capable of concentrating the contact loads. The combination of the rigid and flexible protuberances 40 and 42 provides all of these advantages simultaneously. For example, the fingers 24 and 26 can achieve an initial grasp with the softer protuberances 40 to stabilize the grasp, then follow up with the harder protuberances 42 to increase the gripping force and engage hard regions of the grasp object. If the grasp object is fragile, the apparatus can apply a grip using just the softer protuberances 40. These advantages are enhanced by the load and position sensing capacity of the apparatus. As shown most clearly in FIG. 2, a position sensor 23 is included, as well as a load sensor 25, all as known in the art. The load sensor 25 is supported between bearings 27. The load and position sensors 23 and 25 work cooperatively with the rigid and flexible protuberances 40 and 42 to enable the apparatus 20 to secure a more stable grip upon a grasp object without crushing or otherwise deforming the object.

Figure 5B:
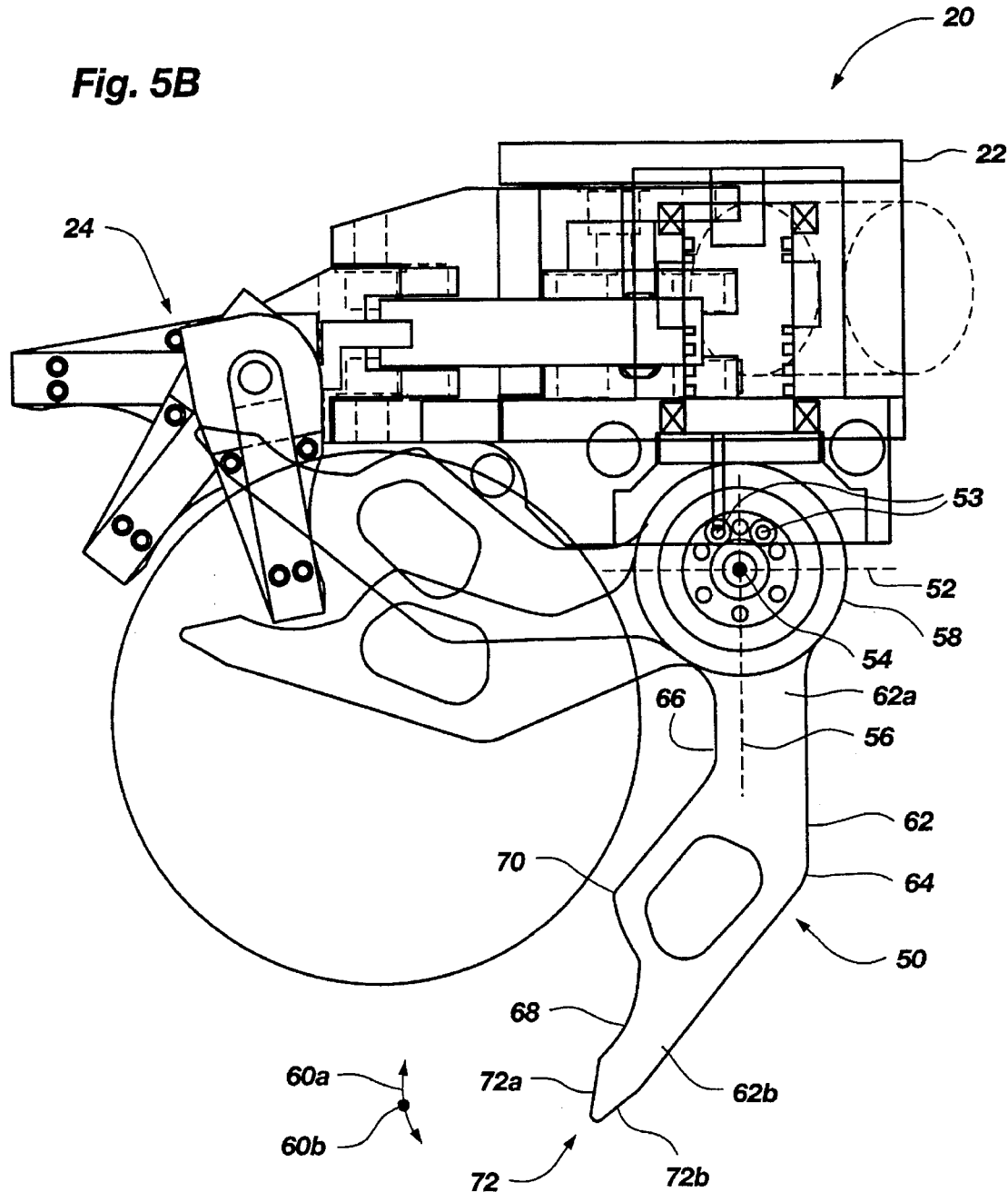
FIG. 5B is a side view of a robotic grasping apparatus including the thumb of FIG. 5A and the finger tip of FIG. 3, and showing stages of movement of said thumb and finger tip.

Referring to FIGS. 5A and 5B, a thumb 50 is pivotally joined to the base 22 to pivot about two axes 52 and 54 (FIG. 5B). Both of the axes 52 and 54 extend laterally relative to the long axis 56 of the thumb 50 and each is oriented generally at a right angle to the other. The pivoting mechanism of the thumb 50 includes a spherical yoke 58 which pivots about the axes 52 and 54 and involves standard mounting techniques and structure. This provides the thumb 50 with two degrees of freedom of movement as indicated by arrows 60a and 60b (FIGS. 5A, 5B and 6), i.e., normal to the plane of movement of the fingers 24 and 26, and parallel to said plane of movement. Effecting the pivoting of the thumb 50 may be carried out in any conventional fashion.

The thumb 50 comprises an elongate, partially angled bar 62 having a fixed or base end 62a and a free end 62b. The bar 62 extends from the base end 62a a certain distance to an elbow 64 and then from said elbow 64 at a slight angle, preferably about twelve degrees, to the free end 62b. Formed on the bar 62 and facing the plane of movement of the fingers are first and second concave surfaces 66 and 68. The first concave surface 66 is formed in the base end 62a and the second concave surface 68 is formed in the free end 62b. A hump 70 formed on the bar 62 separates the concave surfaces 66 and 68. The free end 62b of the bar 62 terminates in angled portions 72a and 72b which form a distal end or tip, designated at 72.

The combination of the angled portions 72a and 72b, the tip 72 and the second concave surface 68 increase the effectiveness of the gripping apparatus 20 in grasping and lifting objects from a surface. Moreover, the bend at the elbow 64 allows the angled portion 72a and the second concave section 68 to align with the tip sections 34 to thereby achieve effective pinch grasps. The angled portion 72a is especially useful in pushing objects in the direction of the tip sections 34 when said tip sections are pivoted downward into approximately fifty and one hundred degree positions, as shown in FIG. 5B.

The thumb 50 is moveable so that the distal end 72 may make contact at several of its surfaces with surfaces of the fingers 24 and 26 to thereby grip objects of various shapes and sizes. For example, the tip 72 is moveable into contact with the other ends 28b of the base sections 28 of the fingers 24 and 26 when pivoted toward the plane of movement of said fingers. This enables an object to be held between the concave surface 66 of the thumb 50 and one or both fingers 24 and 26, or between the concave surface 68 and one or both fingers, depending on the size and shape of the object. The hump 70 provides additional structure for gripping an object between the thumb 50 and one or both fingers 24 and 26. It is to be understood that the thumb 50 may comprise may different shapes and embodiments, and is therefore not to be limited to the specific shape shown in the accompanying figures.

The combination of the parallel two-jaw grip of the fingers 24 and 26 with the two-degree-of-freedom thumb 50 enables the apparatus 20 to achieve various cradling grasps. It will be appreciated that a grasping apparatus having only pinching capacity must rely solely upon frictional contact normal to a grasp object in order to constrain and manipulate it. The force of such a grip is entirely a function of the frictional forces between the grasping apparatus and the object, resulting in deformation and/or fracture of deformable and frangible objects. However, the present combination enables the fingers 24 and 26 and the thumb 50 to wrap around and cradle a grasp object, as shown in the non-limiting illustrations of FIGS. 10 and 12. The cradling capacity combines cooperatively with the load and position sensors 23 and 25 and the rigid and flexible protuberances 40 and 42 to enable the apparatus 20 to conform around and constrain a frangible object without breaking it, such as a light bulb. Frangible, brittle objects such as light bulbs do not give or deform before breaking, preventing the prior art pinching grips from consistently constraining such objects without fracturing them.

Figure 10:
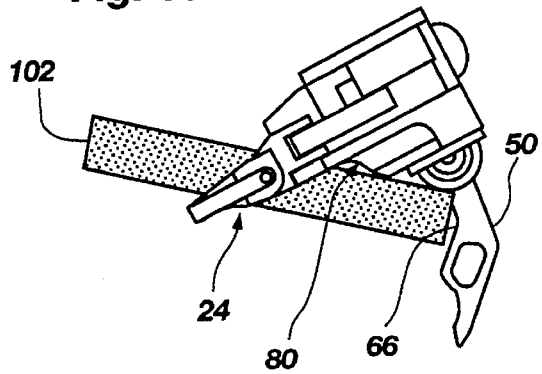
FIG. 10 is a graphic representation of the apparatus holding an elongate bar between the fingers and a concave section of the thumb.
Figure 12:
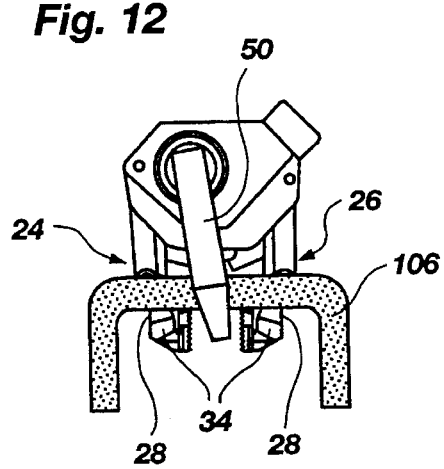
FIG. 12 is a graphic representation of the apparatus holding a handle such as a suitcase handle.

It will be appreciated that the cradling capacity of the apparatus 20 can be accomplished without pivoting of the tip sections 34 such as in FIG. 10, or with pivoting of said tip section 34 as in FIG. 12. A key advantage to the cradling capacity of the apparatus 20 is that the gripping force is not merely a function of the coefficients of kinetic friction of the grasp object and the gripping fingers of a pinch grip; rather, the gripping force is a function of the strength of the robotic arm, which is likely much stronger than the mere friction of a prior art pinch grip.

In addition to the active degrees of freedom of the fingers 24 and 26 and the thumb 50 as heretofore described, the apparatus 20 offers additional advantages of passive degrees of freedom. Referring now to FIG. 6, the base 22 can be viewed as serving the function of a palm of a hand, said base including a palm portion 80 and upper and lower portions 82 and 84, respectively. The fingers 24 and 26 are thus intercoupled to the upper portion 82 by the link connectors 30a and 30b. The fingers 24 and 26 and the thumb 50 can selectively position a grasp object against certain portions of the palm portion 80 to enhance the stability and balance of the grip. In this manner, the palm portion 80 accomplishes a kind of passive degree of freedom in cooperation with the active fingers 24 and 26 and thumb 50. Inspection of FIGS. 5A, 10 and 15 serves to indicate just a few non-limiting examples of the many ways in which the fingers 24 and 26 and thumb 50 can cooperate with the palm portion 80 to establish a stable, balanced robotic grasp.

The palm portion 80 includes a concave area 86 facing the thumb 50 when said thumb 50 is pivoted toward the plane of movement of the fingers 24 and 26. The concave area 86 extends between first and second opposing ends 86a and 86b in a direction generally parallel to the plane of movement of the fingers 24 and 26. A first side 86c of the concave area 86 extends between said ends 86a and 86b and comprises a V-shaped notch for contacting objects held between the thumb 50 and said concave area 86 to thereby align said objects in a direction generally normal to the plane of movement of the fingers 24 and 26. The V-shaped notch of the first side 86c is also useful for aligning objects held only between the fingers 24 and 26. The concave area 86 further includes first and second concave side areas 88 and 90 extending from the first and second opposing ends 86a and 86b, respectively. These concave side areas 88 and 90 are useful for gripping objects with the thumb 50, and they are preferably located different distances from said thumb 50 to allow objects having a wider range of sizes to be gripped.

An advantage of the present invention is that the thumb 50 is modular in that it may be removed and reattached as needed. The thumb 50 is removably secured to the apparatus 20 with screws 53 as shown in FIG. 5B. It will be appreciated that certain applications may require only the services of the parallel two-jaw grip of the fingers 24 and 26, in which the thumb 50 would only encumber the application. The thumb 50 can be removed for such applications simply by removing the screws 53 and extracting the thumb 50.

With the apparatus of FIGS. 1–6, a versatile grasping and holding robotic implement is provided. This apparatus utilizes a removable thumb pivotable in two degrees of freedom, and two fingers moveable back and forth within a plane and having tips which are pivotable generally normal to the plane of movement of the fingers. The palm portion 80 formed in the base 22 assists in holding and aligning elongate objects.

FIGS. 7–15 are graphic representations of the apparatus of FIGS. 1–6 illustrating various objects which can be grasped and the manner in which they can be grasped.

Figure 7:
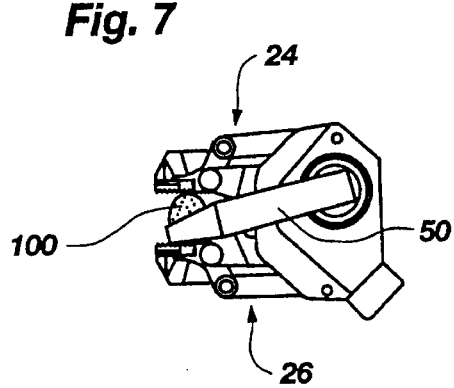
FIG. 7 is a graphic representation of the apparatus in a three point pinch hold of a small object between the thumb and the fingers.

FIG. 7 shows a three-point pinch grasp in which a small three dimensional object 100 is held between the thumb 50 and the fingers 24 and 26. This grasp is similar to a human hand pinching an object using the index finger, middle finger and opposing thumb. This grasp is a somewhat more stable way of holding smaller objects than that shown in the FIG. 8 grasp below (even though the object shown in FIG. 7 is the same size as that shown in FIG. 8).

Figure 8:
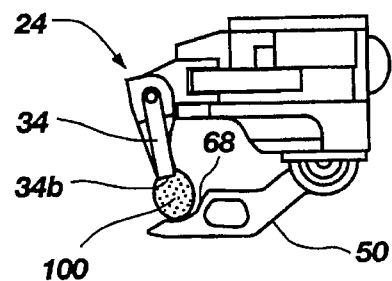
FIG. 8 is a graphic representation of the apparatus in a three point pinch hold of a small object between the thumb and the finger tips.

FIG. 8 shows another, less stable three-point pinch grasp in which the small object 100 is held between the second concave surface 68 of the thumb 50 and the distal ends 34b of the finger tip sections 34.

Figure 9:
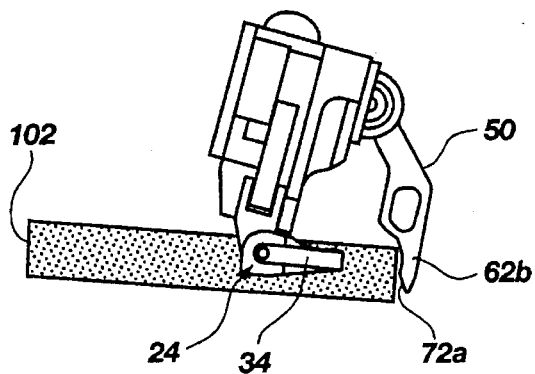
FIG. 9 is a graphic representation of the apparatus holding an elongate bar between downwardly extended finger tips and the thumb.

FIG. 9 shows an elongate bar 102 being held in a three-point grip between the fingers 24 and 26 and the angled portion 72a of the free end 62b of the thumb 50. The tip sections 34 of the fingers 50 are held in a downward pivoted position by the ball detent apparatus 36 (shown in FIG. 1A) in order to secure a more stable grip of the bar 102.

FIG. 10 shows the elongate bar 102 in a three-point grip involving the first concave surface 66 of the thumb 50.

Figure 11:
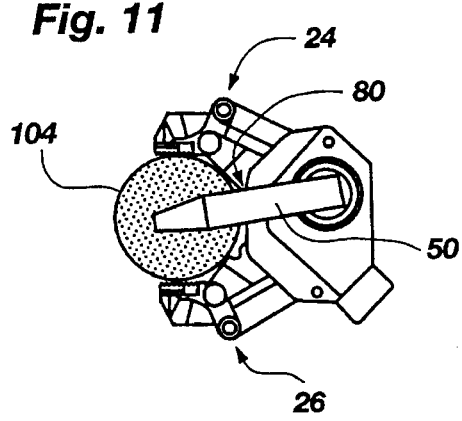
FIG. 11 it is a graphic representation of the apparatus holding a ball with the finger tips downwardly extended.

FIG. 11 shows a spherical grasp in which a ball 104 is held between the two fingers and thumb, but more rearwardly (and against the palm 80) than with the three-point pinches of FIG. 7–8. It will be appreciated that this grip may alternatively be used to grasp a cylindrical rod instead of the spherical ball 104.

FIG. 12 shows a type of loop grasp, for holding suitcase handles, mug handles, telephone receivers, etc., in which a handle 106 is held by the thumb 50 against the base sections 28 of the fingers 24 and 26. Depending on the positioning of the fingers and thumb, the loads can be supported by the second concave section 68 (see FIGS. 5A and 5B) of the thumb 50 and/or the tip section 34 of the finger 24 and 26 so that the lifting capability is independent of the clamping force provided by the thumb 50.

Figure 13:
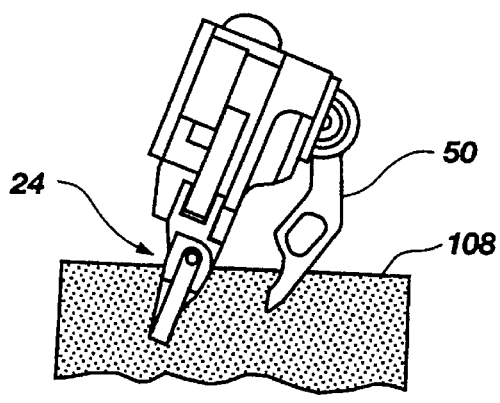
FIG. 13 is a graphic representation of the apparatus holding a thin sheet between the fingers and laterally against the thumb.

FIG. 13 shows a lateral-pinch grasp in which a sheet of material 108 such as a file folder and the like is held between the fingers 24 and 26 and laterally against a side of the thumb 50. This grasp is especially suitable for holding cards or other flat articles when such cards are to be inserted into and removed from locations where the edges of the cards are accessible.

Figure 14:
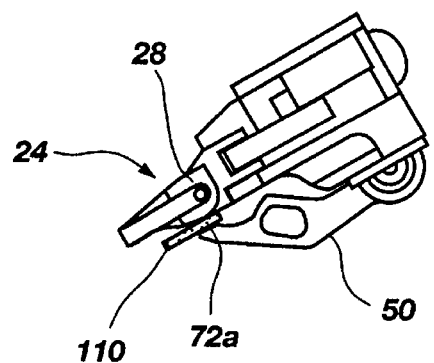
FIG. 14 is a graphic representation of the apparatus holding a thin disc such as a coin between the fingers and the thumb.

FIG. 14 shows a pinch grasp of a thin disc 110 such as a coin and the like between the angled portion 72a of the thumb 50 and the base section 28 of one or both fingers.

Figure 15:
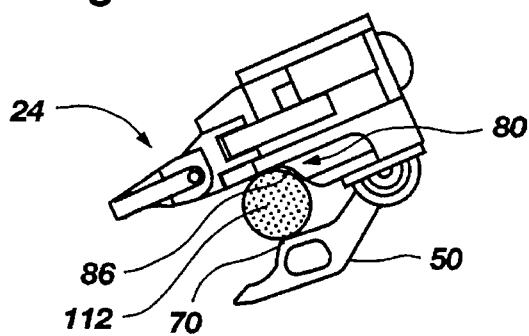
FIG. 15 is a graphic representation of the apparatus holding a round object between a hump portion of the thumb and the fingers.

FIG. 15 shows a grip of a small spherical object 112 such as a ball bearing and the like held between the concave area 86 of the palm 80 and the hump 70 of the thumb 50. It will be appreciated that this grip may alternatively be used to grasp a cylindrical rod instead of the spherical object 112.

Referring now to FIGS. 16–18, the advantages of a rotor actuator with a one-piece housing will now be discussed. A rotor actuator for enabling controlled movement of the thumb 50 of FIGS. 5–15 is designated generally at 120 in FIGS. 16–18. A one-piece housing 122 includes a surrounding wall 124 having an interior surface 126 defining a shaft enclosure 128 therein. A rotatable shaft 130 includes an annular channel 132 formed around the exterior thereof so as to circumscribed said shaft 130. The annular channel 132 is defined by a bottom wall 134 and opposing side walls 136. First and second rotating vanes 138 are configured for fixed attachment to the bottom wall 134 of the annular channel 132 so as to extend away from said bottom wall into said annular channel. First and second stationary vanes 140 (FIG. 17) are configured for insertion into the annular channel 132 and for fixed attachment to the interior surface 126 of the housing 122 so as to extend away from said interior surface into said annular channel.

The rotor actuator 120 can be assembled as follows. The vanes 138 and 140 are inserted into the annular channel 132 of the shaft 130 in the direction indicated by arrows A so as to reside loosely with said annular channel 132. The shaft 130 is then inserted into the shaft enclosure 128 in an axial direction as indicated by arrow B, such that the bottom wall 134 faces the interior surface 126 of said housing 122, such that said annular channel 132 is closed off by said interior surface 126 to define an annular cavity.

The vanes 138 and 140 can be conveniently secured to the shaft 130 and the housing 122, respectively, with pins 139 (or screws, bolts and the like). One way of accomplishing this is as follows. A throughbore 142 in one of the rotating vanes 138 is brought into alignment with a throughbore 144 in the housing 122. A pin 139 is inserted through said throughbore 144 of the housing (and thus in the radial direction) and partway into the throughbore 142 of the rotating vane to maintain the respective throughbores 142 and 144 in alignment. The shaft 130 is rotated until an aperture 146 therein is brought into alignment with the aligned throughbores 142 and 144. The pin 139 is further inserted into the aperture 146 until said pin 139 resides simultaneously within just the throughbore 142 of the rotating vane 138 and the aperture 146 of the shaft 130. The pin 139 can be secured therein in any manner known in the art.

The attached rotating vane is useable to nudge the remaining rotating vane and the stationary vanes 140 one by one into alignment with one of the throughbores 144 of the housing to enable attachment of the remaining rotating vane to the shaft 130 in the manner described above, and to enable attachment of the stationary vanes 140 to the housing 122 as shown in FIG. 17. Each stationary vane 140 is attached by a pin 139 which resides simultaneously in a throughbore 144 of the housing 122 and in an aperture 148 in the stationary vane 140.

With the rotor actuator 120 assembled as described and shown, an annular cavity is defined by the walls 134 and 136 of the annular channel 132, and by the interior surface 126 of the housing 122. Sealing members (not shown) can be used as known in the art to hermetically seal exterior portions of the rotating and stationary vanes 138 and 140 relative to the defining walls and surfaces of the annular cavity, to thereby form hydraulic pressure chambers 150 within said cavity.

Any method or apparatus known in the art for introducing/retracting hydraulic fluid into/out of the pressure chambers 150 can be used to produce hydraulic pressure in the chambers 150 to thereby force movement of the rotating vanes in the directions of arrows D to cause the shaft 130 to rotate. For example, hydraulic fluid could be pumped through axial holes 152 of the shaft 130 (FIG. 17) and forced into the pressure chambers 150 through radial passages 154 (FIG. 17) to force clockwise rotation of the shaft 130 as depicted in FIG. 17. Counterclockwise rotation could be accomplished in any number of ways. For example, the hydraulic fluid can be retracted through the holes 152 and 154 under negative pressure. Or, additional hydraulic fluid could be pumped into the chambers 151 under positive pressure to force movement of the rotating vanes 138 and shaft 130 in the desired counterclockwise direction. It is to be understood that any manner or method of utilizing hydraulic pressure can be used to cause selective, controlled rotation of the shaft 130. The rotor actuator 120 is operably connected to the thumb 150 to enable selective, controlled movement of the thumb 50, in cooperation with the position and load sensors 23 and 25. Two rotor actuators 120 may be used to accomplish movement of the thumb 50 in two degrees of freedom.

The rotor actuator 120 made in accordance with the present invention offers many advantages over known actuators, including, but not limited to, the following.

Fewer Parts. The rotor actuator 120 requires fewer parts. The combination disclosed enables the rotor actuator 120 to be formed from two main pieces, the one-piece housing 122 and the shaft 130. Many prior art actuators require a two-piece housing-and-plate combination, wherein the plate fits over one of the open ends of the housing to cooperatively "sandwich" the shaft into position. Such plates are generally secured to the housing with screws extending axially into the walls of the housing.

Easier Assembly. The rotor actuator 120 is easier to assemble, and requires fewer steps, than assembly of many prior art actuators. The prior art actuators utilizing a two-piece housing require the extra step of bolting the plate onto the housing. The plate often requires thirty-two bolts for adequate strength, which requires significant additional assembly time. As noted above, the invention is unique in that the shaft 130 can be rotatably manipulated by an assembler to cause an attached rotating vane to consecutively nudge other vanes into alignment with a throughbore 144 of the housing for convenient assembly of rotating and stationary vanes.

No Axial Pressure Load On The Housing. Since only the shaft 130 defines the annular channel 132, the entire axial load produced within the pressure chambers 150 is absorbed by the shaft 130. None of the axial pressure load is applied to the housing 122, as opposed to the prior art two-piece housings wherein the housing-and-plate combination defines the annular void space so that the housing must absorb the axial pressure loads. Actuator shafts are often made from a stronger material than the housings; for example, a steel shaft within an aluminum housing. The shaft is usually made of steel so that it can be smaller for design purposes, and because it must take the torsional loads. The present invention utilizes the superior strength of the shaft by taking the axial load away from the housing and putting it onto the shaft.

Reduced Overall Material Volume of the Actuator. As described above, the stationary vanes 140 are attached to the housing 122 with radially-directed pins 139. Stationary vanes in many prior art actuators are secured with axially-oriented fasteners, in addition to having a plate member secured to a housing body with axial-oriented screws extending axially into the housing walls as part of a two-piece housing. Since the screws securing the plate to the housing body of the prior art actuators are directed into the housing walls, the housing body must be much larger in order to have enough material strength to withstand the loads. Since the housing 122 of the present invention does not absorb the axial pressure loads and need not have axially-oriented screws installed into its walls, it can be made of much less material to achieve a given actuator output strength. Accordingly, the ratios of power output/ actuator volume, and power output/actuator weight are reduced by the present invention.

It will be appreciated that the rotor actuator 120 shown in FIGS. 16–17 is a double-vaned rotor actuator, because there are two rotating vanes 138. It is to be understood that it is also within the scope of the present invention to make a single-vaned rotor actuator by utilizing just one rotating vane 138 and at least one stationary vane 140.

It is to be understood that any sealing means may be used to hermetically seal exterior portions of the vanes 138 and 140 to the defining walls and surfaces of the annular cavity in order to establish the necessary seals. The sealing means must enable the rotating vanes to be movably sealed within the annular cavity, such that movement of the rotating vanes does not break or otherwise diminish the integrity of the seal.

It is to be further understood that many alternative embodiments of the rotor actuator 120 are within the scope of the invention. Referring now to FIG. 18, it will be appreciated that the housing 122 can be used to define the annular channel 132 instead of the shaft 130. In this embodiment, the housing 122 will absorb the axial load of the hydraulic pressure instead of the shaft 130. However, it will be appreciated that the ratios noted above are still reduced by the embodiment of FIG. 18, i.e. the ratios of power output/actuator volume, and power output/actuator weight. Because of the one-piece, unibody nature of the housing 122 in FIG. 18, no screws are needed to secure a plate to the housing walls, which would require the housing to be larger and heavier.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. Robotic gripping apparatus comprising:

a support base, and first and second fingers attached at proximal ends to the support base to extend forwardly therefrom, and selectively moveable in a plane toward or away from one another, each of said fingers including a base section attached at one end to the support base, and a tip section pivotally attached at a pivot end to the other end of the base section and pivotable downwardly in a direction generally normal to the plane of movement of the fingers, and a facing side facing the other finger, each facing side including a first plurality of substantially rigid protuberances projecting toward the other facing side, and a second plurality of substantially flexible, resilient protuberances projecting toward the other facing side.

2. Robotic gripping apparatus as in claim 1 further including means for attaching the fingers to the support base and for moving the fingers toward or away from one another such that gripping sides of the fingers remain generally parallel to one another.

3. Robotic gripping apparatus as in claim 2 wherein said attaching and moving means comprises first linkage means intercoupling the first finger with the support base, and moveable to cause the first finger to move toward or away from the second finger, second linkage means intercoupling the second finger with the support base, and moveable to cause the second finger to move toward or away from the first finger, piston means having a piston rod selectively moveable generally linearly in a back and forth fashion, and a connecting link pivotally connected to the first linkage means and second linkage means and pivotally connected to the piston rod to move when the piston rod is moved and thereby cause the first and second linkage means, and first and second fingers respectively, to move.

4. Robotic gripping apparatus as in claim 3 wherein each said first and second linkage means comprises a pair of parallel bars pivotally coupled between a respective finger and the support base, to pivot in parallel, one of each pair of bars being disposed adjacent one another in the plane of movement of the fingers, and wherein said connecting link is pivotally coupled to said adjacent bars to move along a locus which extends between the two adjacent bars at an angle with the midline between the adjacent bars.

5. Robotic gripping apparatus as in claim 1 further including first and second locking means for respectively locking the tip sections of the first and second fingers in a plurality of different positions of the tip sections pivoted downwardly from the plane of movement of the fingers.

6. Robotic gripping apparatus as in claim 5 wherein said locking means each comprises a ball detent means disposed at a respective pivot end of a tip section and respective other end of a base section.

7. Robotic gripping apparatus as in claim 1 wherein said second protuberances are interleaved with said first protuberances, and said second protuberances project farther toward the other facing side than said first protuberances.

8. Robotic gripping apparatus as in claim 7 wherein said first protuberances are each shaped to terminate generally in a point, and wherein said second protuberances are each shaped to terminate generally in a blunt surface.

9. Robotic gripping apparatus as in claim 8 wherein said first protuberances are made of a metal alloy, and wherein said second protuberances are made of a non-skid polymer composition.

10. Robotic gripping apparatus as in claim 1 further including elongate thumb means pivotally attached at a proximal end to the support base to pivot a distal end toward and away from the plane of movement of the fingers, and pivot in a plane normal to the plane of movement of the fingers.

11. Robotic gripping apparatus as in claim 10 wherein the distal end of the thumb means extends about to the other ends of the base sections of the fingers, when pivoted toward the plane of movement of the fingers.

12. Robotic gripping apparatus as in claim 11 wherein said thumb means includes a gripping side which faces the plane of movement of the fingers when pivoted theretoward, said gripping side including a first concave section at the distal end to contact objects held between the thumb means and fingers.

13. Robotic gripping apparatus as in claim 12 wherein said gripping side of the thumb means further includes a second concave section between the first concave section and the proximal end of the thumb means to contact objects held between the thumb means and concave area of the support base.

14. Robotic gripping apparatus as in claim 10 wherein said thumb means includes a gripping side which faces the plane of movement of the fingers when pivoted theretoward, said gripping side including first and second generally concave gripping surfaces disposed near the proximal end and distal end respectively and separated by a hump, for holding an object against the support base and fingers respectively.

15. Robotic gripping apparatus as in claim 1 further including elongate thumb means pivotally attached at a proximal end to the support base to pivot selectively about either of two axes which are generally at right angles to one another and which both extend laterally relative to the long axis of the thumb means.

16. Apparatus for grasping objects comprising:

hand means having an upper portion, a lower portion, and a palm portion between said upper and lower portion, a pair of fingers attached at proximal ends to the upper portion of the hand means, at least one of which is moveable selectively toward or away from the other finger, each of said fingers including a facing, gripping side, each of said sides comprising a first plurality of substantially rigid projections extending from said each side outwardly, and a second plurality of substantially flexible, resilient projections, interleaved with said first projections and extending from said each side outwardly a greater distance than said first projections, said second projections for contacting and holding lower weight, more fragile objects, and said first projections for holding higher weight, less fragile objects.

17. Apparatus as in claim 16 wherein said first projections terminate generally in a point, and second projections terminate generally in a plane or convex end.

18. Apparatus as in claim 17 wherein said first projections are generally pyramidal in shape.

19. Apparatus as in claim 17 wherein said first projections are constructed of a metal alloy, and wherein said second projections are constructed of a non-skid polymer composition.

20. Apparatus as in claim 16 further including means for selectively causing the fingers to move toward one another simultaneously or away from one another simultaneously.

21. Apparatus as in claim 20 wherein said fingers are disposed generally parallel to one another and wherein the means for selectively causing the fingers to move operates to move said fingers such that gripping sides of said fingers remain generally parallel when moved.

22. Apparatus as in claim 16 wherein said at least one moveable finger is selectively moveable in a plane toward or away from the other finger, each finger including a base section attached at one end to the upper portion of the hand means, and a tip section pivotally attached at a pivot end to the other end of the base section and pivotable downwardly in a direction generally normal to the plane of movement of said at least one moveable finger.

23. Apparatus as in claim 16 further including elongate thumb means pivotally attached at a proximal end to the lower portion of the hand means to pivot a distal end toward and away from the fingers.

24. Robotic gripping apparatus comprising:

hand means having an upper portion and a lower portion;

first and second fingers;

first and second linkage means intercoupling the first and second fingers, respectively, with the upper portion of the hand means such that said fingers extend forwardly therefrom, said first and second linkage means being moveable to cause the fingers to move toward or away from each other in a plane, piston means disposed on the upper portion of the hand means and having a piston rod selectively movable generally linearly in a back and forth fashion, a connecting link pivotally connected to the first linkage means and second linkage means, and pivotally connected to the piston rod to move when the piston rod is moved and thereby cause the first and second linkage means, and the first and second fingers respectively, to move, and wherein each said first and second linkage means is pivotally coupled at a first end thereof to its corresponding finger and at an opposing second end thereof to the upper portion of the hand means, and wherein the connecting link is respectively pivotally coupled at opposing ends thereof to the first and second linkage means in such a manner that when the piston rod is moved in a linear motion, the connecting link causes the first and second fingers to move within a plane such that gripping surfaces of said first and second fingers remain in a parallel orientation relative to one another;

elongate thumb means pivotally attached at a proximal end to the lower portion of the hand means to extend forwardly therefrom and pivot a distal end toward and away from the plane of movement of the fingers, and wherein the hand means includes a palm portion formed between the upper and lower portions, said palm portion having a concave area which faces the thumb means when said thumb means is pivoted toward the plane of movement of the fingers, and wherein the thumb means includes a gripping side which faces the plane of movement of the fingers when pivoted theretoward, said gripping side including a concave section to contact objects held between the thumb means and the concave area of the palm portion.

25. Robotic gripping apparatus as in claim 24 wherein the concave area of the palm portion extends between first and second opposing ends thereof in a direction generally parallel to the plane of movement of the fingers and includes a first side extending between said ends and comprising a V-shaped notch to contact objects held between the thumb means and the concave area and to align said objects in a direction generally normal to the plane of movement of the fingers.

26. Robotic gripping apparatus as in claim 24 wherein the palm portion further includes first and second concave side areas extending from first and second opposing ends of the concave area, respectively, to enable objects to be gripped between the gripping side of the thumb means and said concave side areas.

27. Robotic gripping apparatus as in claim 26 wherein the concave side areas of the palm portion are located different distances from the thumb means to enable objects having a wider range of sizes to be gripped between said concave side areas and the thumb.

28. Robotic gripping apparatus comprising:

hand means having an upper portion and a lower portion, first and second fingers wherein each of the fingers includes a facing, gripping side, each of said sides comprising a first plurality of substantially rigid projections extending from said each side outwardly, and a second plurality of substantially flexible, resilient projections, interleaved with said first projections and extending from said each side outwardly a greater distance than said first projections, said second projections for contacting and holding lower weight, more fragile objects, and said first projections for holding higher weight, less fragile objects;

first and second linkage means intercoupling the first and second fingers, respectively, with the upper portion of the hand means such that said fingers extend forwardly therefrom, said first and second linkage means being moveable to cause the fingers to move toward or away from each other in a plane, piston means disposed on the upper portion of the hand means and having a piston rod selectively moveable generally linearly in a back and forth fashion, and a connecting link pivotally connected to the first linkage means and second linkage means, and pivotally connected to the piston rod to move when the piston rod is moved and thereby cause the first and second linkage means, and first and second fingers respectively, to move.

29. Apparatus as in claim 28 wherein said first projections terminate generally in a point, and second projections terminate generally in a plane or convex end.

30. Apparatus as in claim 29 wherein said first projections are generally pyramidal in shape.

31. Apparatus as in claim 29 wherein said first projections are constructed of a metal alloy, and wherein said second projections are constructed of a non-skid polymer composition.

32. Robotic gripping apparatus comprising hand means having an upper portion and a lower portion, first and second fingers;

first and second linkage means intercoupling the first and second fingers, respectively, with the upper portion of the hand means such that said fingers extend forwardly therefrom, said first and second linkage means being moveable to cause the fingers to move toward or away from each other in a plane, piston means disposed on the upper portion of the had means and having a piston rod selectively movable generally linearly in a back and forth fashion, a connecting link pivotally connected to the first linkage means and second linkage means, and pivotally connected to the piston rod to move when the piston rod is moved and thereby cause the first and second linkage means, and the first and second fingers respectively, to move, and wherein each said first and second linkage means is pivotally coupled at a first end thereof to its corresponding finger and at an opposing second end thereof to the upper portion of the hand means, and wherein the connecting link is respectively pivotally coupled at opposing ends thereof to the first and second linkage means in such a manner that when the piston rod is moved in a linear motion, the connecting link causes the first and second fingers to move within a plane such that gripping surfaces of said first and second fingers remain in a parallel orientation relative to one another, elongate thumb means pivotally attached at a proximal end to the lower portion of the hand means to extend forwardly therefrom and pivot selectively about either of two axes which are generally at right angles to one another and which both extend laterally relative to the long axis of the thumb means; and at least one rotor actuator attached to the thumb means and configured to cause controlled pivotal movement of said thumb means, said rotor actuator including:

a one-piece housing including a surrounding wall having an interior surface defining a shaft enclosure therewith;

rotatable shaft means including a shaft body having a central axis, at least a portion of the shaft body being configured for insertion into the shaft enclosure of the housing, said shaft means including an annular channel formed around an exterior of the shaft body so as to circumscribe the central axis of the shaft body, said annular channel being defined by a bottom wall and opposing side walls such that when said portion of said shaft means is inserted into said shaft enclosure of the housing, the bottom wall faces the interior surface of the housing such that said annular channel is closed off by said interior surface to define an annular cavity;

at least one stationary vane for fixed attachment to the interior surface of the housing so as to project into the annular cavity toward the bottom wall of the annular channel;

at least one rotating vane for fixed attachment to the bottom wall of the annular channel so as to project into the annular cavity toward the interior surface of the housing;

sealing means for hermetically sealing exterior portions of the stationary vane and the rotating vane relative to the walls and surfaces of the annular cavity to thereby define at least one hydraulic pressure chamber within said annular cavity; and means for selectively introducing hydraulic fluid into the hydraulic pressure chamber to thereby produce hydraulic pressure therein to force movement of the rotating vane to thereby cause the shaft to rotate.

33. Robotic gripping apparatus comprising hand means having an upper portion and a lower portion, first and second fingers;

first and second linkage means intercoupling the first and second fingers, respectively, with the upper portion of the hand means such that said fingers extend forwardly therefrom, said first and second linkage means being moveable to cause the fingers to move toward or away from each other in a plane, piston means disposed on the upper portion of the hand means and having a piston rod selectively movable generally linearly in a back and forth fashion, a connecting link pivotally connected to the first linkage means and second linkage means, and pivotally connected to the piston rod to move when the piston rod is moved and thereby cause the firs and second linkage means, and the first and second fingers respectively, to move, and wherein each said first and second linkage means is pivotally coupled at a first end thereof to its corresponding finger and at an opposing second end thereof to the upper portion of the hand means, and wherein the connecting link is respectively pivotally coupled at opposing ends thereof to the first and second linkage means in such a manner that when the piston rod is moved in a linear motion, the connecting link causes the first and second fingers to move within a plane such that gripping surfaces of said first and second fingers remain in a parallel orientation relative to one another, elongate thumb means pivotally attached at a proximal end to the lower portion of the hand means to extend forwardly therefrom and pivot selectively about either of two axes which are generally at right angles to one another and which both extend laterally relative to the long axis of the thumb means; and at least one rotor actuator attached to the thumb means and configured to cause controlled pivotal movement of said thumb means, said rotor actuator including:

rotatable shaft means having an exterior wall;

a one-piece housing including a surrounding wall having a central axis and an interior surface defining a shaft enclosure configured to receive at least a portion of the shaft means, said housing including an annular channel formed around the interior surface so as to circumscribe the central axis of the surrounding wall, said annular channel being defined by a bottom wall and opposing side walls such that when said portion of said shaft means is received into said shaft enclosure of the housing, said bottom wall faces the exterior wall of the shaft means such that said annular channel is closed off by said exterior wall to define an annular cavity;

at least one stationary vane for fixed attachment to the bottom wall of the annular channel so as to project into the annular cavity toward the exterior wall of the shaft means;

at least one rotating vane for fixed attachment to the exterior wall of the shaft means so as to project into the annular cavity toward the bottom wall of the annular channel;

sealing means for hermetically sealing exterior portions of the stationary vane and the rotating vane relative to the walls of the annular cavity to thereby define at least one hydraulic pressure chamber within said annular cavity; and means for selectively introducing hydraulic fluid into the hydraulic pressure chamber to thereby produce hydraulic pressure therein to force movement of the rotating vane to thereby cause the shaft to rotate.

34. A rotor actuator comprising:

a one-piece housing including a surrounding wall having an interior surface defining a shaft enclosure therewith;

rotatable shaft means including a shaft body having a central axis, at least a portion of the shaft body being configured for insertion into the shaft enclosure of the housing, said shaft means including an annular channel formed around an exterior of the shaft body so as to circumscribe the central axis of the shaft body, said annular channel being defined by a bottom wall and opposing side walls such that when said portion of said shaft means is inserted into said shaft enclosure of the housing, the bottom wall faces the interior surface of the housing such that said annular channel is closed off by said interior surface to define an annular cavity;

at least one stationary vane for fixed attachment to the interior surface of the housing so as to project into the annular cavity toward the bottom wall of the annular channel;

at least one rotating vane for fixed attachment to the bottom wall of the annular channel so as to project into the annular cavity toward the interior surface of the housing;

sealing means for hermetically sealing exterior portions of the stationary vane and the rotating vane relative to the walls and surfaces of the annular cavity to thereby define at least one hydraulic pressure chamber within said annular cavity; and means for selectively introducing hydraulic fluid into the hydraulic pressure chamber to thereby produce hydraulic pressure therein to force movement of the rotating vane to thereby cause the shaft to rotate.

35. A rotor actuator as defined in claim 34, wherein the bottom wall of the shaft means and the stationary vane each includes an aperture formed therein, and wherein the rotating vane and the surrounding wall of the housing each includes a throughbore formed therein, the shaft means, housing, rotating vane and stationary vane being selectively moveable to thereby permit the throughbore of the surrounding wall to be aligned with the other bores to enable fastening members to be inserted through said throughbore of the surrounding wall and into the other bores in a radial direction relative to the shaft means, said rotor actuator further comprising:

a first fastening member configured for insertion into the throughbore of the rotating vane and the aperture of the bottom wall of the shaft means so as to reside simultaneously therein to thereby fixedly intercouple said rotating vane and said shaft means such that the rotating vane is confined to rotation in tandem with the shaft means; and a second fastening member configured for insertion into the throughbore of the surrounding wall of the housing and the aperture of the stationary vane so as to reside simultaneously therein to thereby fixedly intercouple said stationary vane and said housing.

36. A rotor actuator as defined in claim 34, wherein said at least one stationary vane comprises two separate stationary vanes, and wherein said at least one rotating vane comprises two separate rotating vanes, to thereby define at least two hydraulic pressure chambers within the annular cavity as part of a double-veined rotor actuator.

37. A rotor actuator comprising:

rotatable shaft means having an exterior wall;

a one-piece housing including a surrounding wall having a central axis and an interior surface defining a shaft enclosure configured to receive at least a portion of the shaft means, said housing including an annular channel formed around the interior surface so as to circumscribe the central axis of the surrounding wall, said annular channel being defined by a bottom wall and opposing side walls such that when said portion of said shaft means is received into said shaft enclosure of the housing, said bottom wall faces the exterior wall of the shaft means such that said annular channel is closed off by said exterior wall to define an annular cavity;

at least one stationary vane for fixed attachment to the bottom wall of the annular channel so as to project into the annular cavity toward the exterior wall of the shaft means;

at least one rotating vane for fixed attachment to the exterior wall of the shaft means so as to project into the annular cavity toward the bottom wall of the annular channel;

sealing means for hermetically sealing exterior portions of the stationary vane and the rotating vane relative to the walls of the annular cavity to thereby define at least one hydraulic pressure chamber within said annular cavity; and means for selectively introducing hydraulic fluid into the hydraulic pressure chamber to thereby produce hydraulic pressure therein to force movement of the rotating vane to thereby cause the shaft to rotate.

38. A rotor actuator as defined in claim 37, wherein the exterior wall of the shaft means and the stationary vane each includes an aperture formed therein, and wherein the rotating vane and the surrounding wall of the housing each includes a throughbore formed therein, the shaft means, housing, rotating vane and stationary vane being selectively moveable to thereby permit the throughbore of the surrounding wall to be aligned with the other bores to enable fastening members to be inserted through said throughbore of the surrounding wall and into the other bores in a radial direction relative to the shaft means, said rotor actuator further comprising:

a first fastening member configured for insertion into the throughbore of the rotating vane and the aperture of the exterior wall of the shaft means so as to reside simultaneously therein to thereby fixedly intercouple said rotating vane and said shaft means such that the rotating vane is confined to rotation in tandem with the shaft means; and a second fastening member configured for insertion into the throughbore of the surrounding wall of the housing and the aperture of the stationary vane so as to reside simultaneously therein to thereby fixedly intercouple said stationary vane and said housing.

39. A rotor actuator as defined in claim 37, wherein said at least one stationary vane comprises two separate stationary vanes, and wherein said at least one rotating vane comprises two separate rotating vanes, to thereby define at least two hydraulic pressure chambers within the annular cavity as part of a double-veined rotor actuator.

* * * * *